United States Patent [19]

Ivanova et al.

[11] Patent Number: 4,666,918
[45] Date of Patent: May 19, 1987

[54] TETRAHYDROISOQUINOLINE DERIVATIVES AND METHOD

[75] Inventors: Nedyalka S. Ivanova; Milka P. Nikolova; Chavdar B. Ivanov; Margarita D. Dryanska; Orhideya B. Zabunova, all of Sofia, Bulgaria

[73] Assignee: TPO "Pharmachim", Sofia, Bulgaria

[21] Appl. No.: 748,554

[22] Filed: Jun. 25, 1985

Related U.S. Application Data

[63] Continuation-in-part of Ser. No. 621,538, Jun. 10, 1984, abandoned.

[30] Foreign Application Priority Data

Jun. 21, 1983 [BG] Bulgaria .................................. 61406

[51] Int. Cl.$^4$ ............................................. A61U 31/47
[52] U.S. Cl. .................................................... 514/307
[58] Field of Search ........................................ 514/307

[56] References Cited

FOREIGN PATENT DOCUMENTS 1114660 5/1968 United Kingdom .
1173719 12/1969 United Kingdom .
27864 of 1968 Japan .

OTHER PUBLICATIONS

The Action of Sympathicomimetic Drugs on Uterine Muscle, P. K. Kloeck.
The Action of Betamimetrics on the Myometrium, R. Czekanowski.
The Administration of Beta-Sympathomimetic Agents in Obstretric Emergencies.
Current Status of Tocolysis Labor Inhibition; Hans Weidinger.
Triquinol, Experimental & Chemical Studies, Clinical Tests–Pharmachim. Bul.
Bulletin of the Institute of Physiology; vol. IX (1965).

Primary Examiner—Stanley J. Friedman

[57] ABSTRACT

The invention relates to tetrahydroisoquinoline derivatives of the Formula

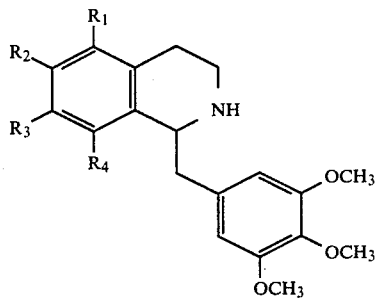

wherein $R_1$, $R_2$, $R_3$ and $R_4$ are each selected from the group consisting of a hydrogen and a hydroxyl group. These derivatives are useful in tocology (obstetrics).

Administration of the inventive compounds induces relaxation of uterine muscles, a property that is particularly useful in cases of second trimester miscarriage, premature birth up to the 37th or 38th week of pregnancy, and during delivery. The compounds are especially useful from the onset of labor up to delivery of the newborn's head, a period which is often accompanied or complicated by frequent, violent, uncoordinated contractions of the uterus. The compounds are also useful in obstetric and gynecological operations, such as a hysterectomy, surgery for acute placental insufficiency, etc.

6 Claims, 10 Drawing Figures

TETRAHYDROISOQUINOLINE DERIVATIVES AND METHOD

RELATED APPLICATION

This in a C-I-P of Ser. No. 621,538, filed June 10, 1984, now abandoned".

The invention relates to tetrahydroisoquinoline derivatives of the Formula

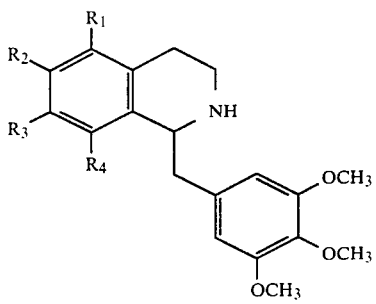

wherein $R_1$, $R_2$, $R_3$ and $R_4$ are each selected from the group consisting of a hydrogen and a hydroxyl group. These derivatives are useful in tocology (obstetrics and gynecology). More particularly, the invention relates to a pharmaceutical composition containing a tetrahydroisoquinoline derivative of Formula I, or a physiologically compatible salt thereof, as the active ingredient.

Administration of the inventive compounds induces relaxation of uterine muscles, a property that is valuable in obstetric and gynecological practice, particularly in cases of second trimester miscarriage, premature birth up to the 37th or 38th week of pregnancy, and during delivery. The compounds are especially useful from the onset of labor up to delivery of the newborn's head, a period which is often accompanied or complicated by frequent, violent, uncoordinated contractions of the uterus. The compounds are also useful in obstetric and gynecological operations, such as a hysterectomy, surgery for acute placental insufficiency, etc.

BACKGROUND OF THE INVENTION

The compound 1-(3,5 dihydrophenyl)-2-[(4-hydroxybenzyl)-ethyl-amino]-ethanol hydrobromide is the active ingredient of "Partusisten," a pharmaceutical composition having a tocolytic effect that is useful in the suppression of premature uterine contraction. A serious disadvantage of this drug is its secondary effect on the cardiovascular system. See, Labor Inhibition Betamimetic Drugs in Obstetrics: F. K. Klock, *The action of Sympathicomimetic Drugs on Uterine Muscle,* Dept. of Gynecology and Obstetrics, RWTH (Achen, FRG: 1977), p. 27; R. Czekanowski, *The Action of Betamimetics on the Myometrium,* Institute of Obstetrics and Gynecology (Bialystok, Poland: 1977), p. 11; and F. Ropke and H. Y. Woraschk, *The Administration of Beta-Sympathomimetic Agents in Obstetric Emergencies,* Martin-Luther-Universitat (Halle, DDR: 1977), p. 235.

SUMMARY OF THE INVENTION

It is an object of the invention to provide a uterine relaxant (tocolytic means) having fewer and less severe side-effects than the known compositions. The compounds of Formula 1 achieve this objective, and also exhibit an unexpectedly high and long-lasting activity. The tetrahydroisoquinoline derivatives of Formula 1 suppress the spontaneous bioelectric and contracting activity of the uterus of pregnant and non-pregnant rabbits.

In suitable therapeutic doses, the present derivatives can be administered to prevent miscarriage, to prevent a dangerously premature birth, and to lessen the throes of childbirth. The compounds can be administered orally or parenterally in a pharmaceutical composition comprising a pill or injection, or they can be administered as suppositories. The active component of the composition (the tetrahydroisoquinoline derivative of Formula 1) is combined with inert pharmaceutical excipients according to known methods.

The compounds may be administered orally in doses ranging from 9 to 20 mg/day. Parenteral administration is in doses of from 1 to 5 kg/min. Suppositories may be dosed at from 1 to 2 mg per day.

The present derivatives are advantageous for a number of reasons. Using 1-(3,5 dihydrophenyl)-2-[(4-hydroxybenzyl)-ethyl-amino]-ethanol hydrobromide as a reference compound (Compound A), the new compounds are stronger and longer-lasting inhibitors of spontaneous contractions in pregnant animals; they decrease basal tonicity in pregnant animals, indicating a strong relaxation of uterine muscle not shown by the reference compound; they act faster than the reference compound; they increase the pulse rate in dogs by half as much as the reference compound; and unlike the reference compound, they do not cause any appreciable deviation in the alkaline-acid parameters of pregnant women (BE, SB, $pCO_2$, $pO_2$) nor do they provoke any tendency toward metabolyte acidose in the first hours after administration. These advantages are of particular importance with regard to the alkaline-acid state of the fetus. Finally, administration of the present compound and tocolytic composition in suppository form provides for improved selective action on uterine muscle.

The tocolytic activity of the compounds of Formula 1, and in particular of the embodiment 1-1-(3,4,5-trimetoxybenzyl)-6,7-dihydroxy-1,2,3,4-tetrahydroisoquinoline, wherein $R_1$ and $R_4$ are hydrogen and $R_2$ and $R_3$ are each a hydroxyl group, (compound $I^a$) in comparison with the reference compound 1-(3,5dihydrophenyl)-2-[(4-hydroxybenzyl)-ethyl-amino]-ethanol hydrobromide (compound A) is demonstrated by a number of drawings and examples. It is understood that these are illustrative, and do not serve to limit the scope of the disclosure and the appended claims.

DETAILED DESCRIPTION

Experiments on Rats

Female rats of the "Vistar" breed were submitted to ovariectomy and after the 17th day were treated with estradiol for 4 days. Muscle strips of the uterus cornis were then isolated and placed in a 36° C. Crebs solution organ bath aerated by 95% $O_2$ and 5% $CO_2$. The contractile activity of the strips was recorded by a microelectrical transducer, Swena SG 4-90, a direct current recorder under an isometric regimen.

Figure 1:
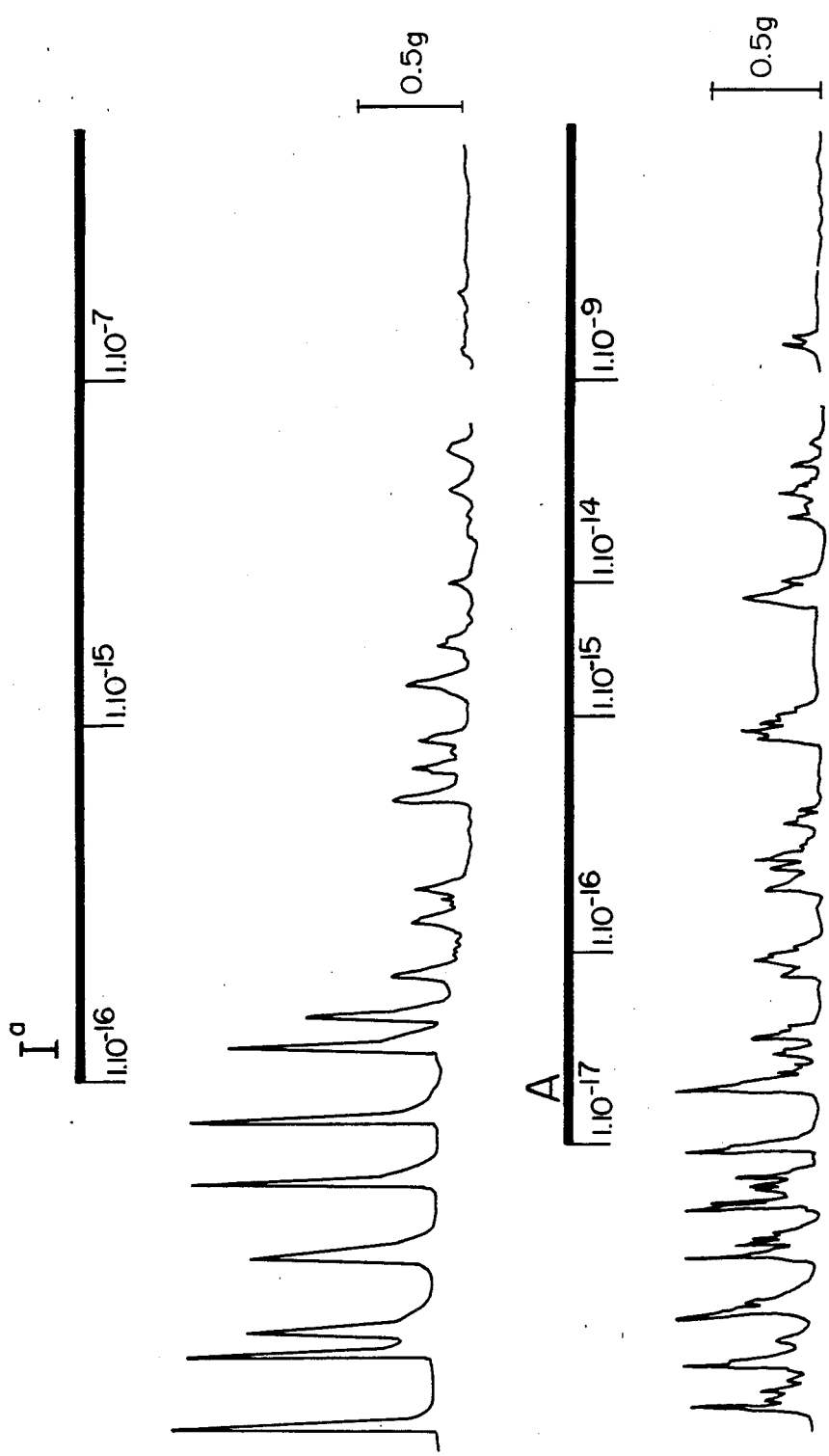
FIG. 1 represents the effect of inventive compound $I^a$ and reference compound A on spontaneous contractions of myometric strips derived from rats.
Figure 2:
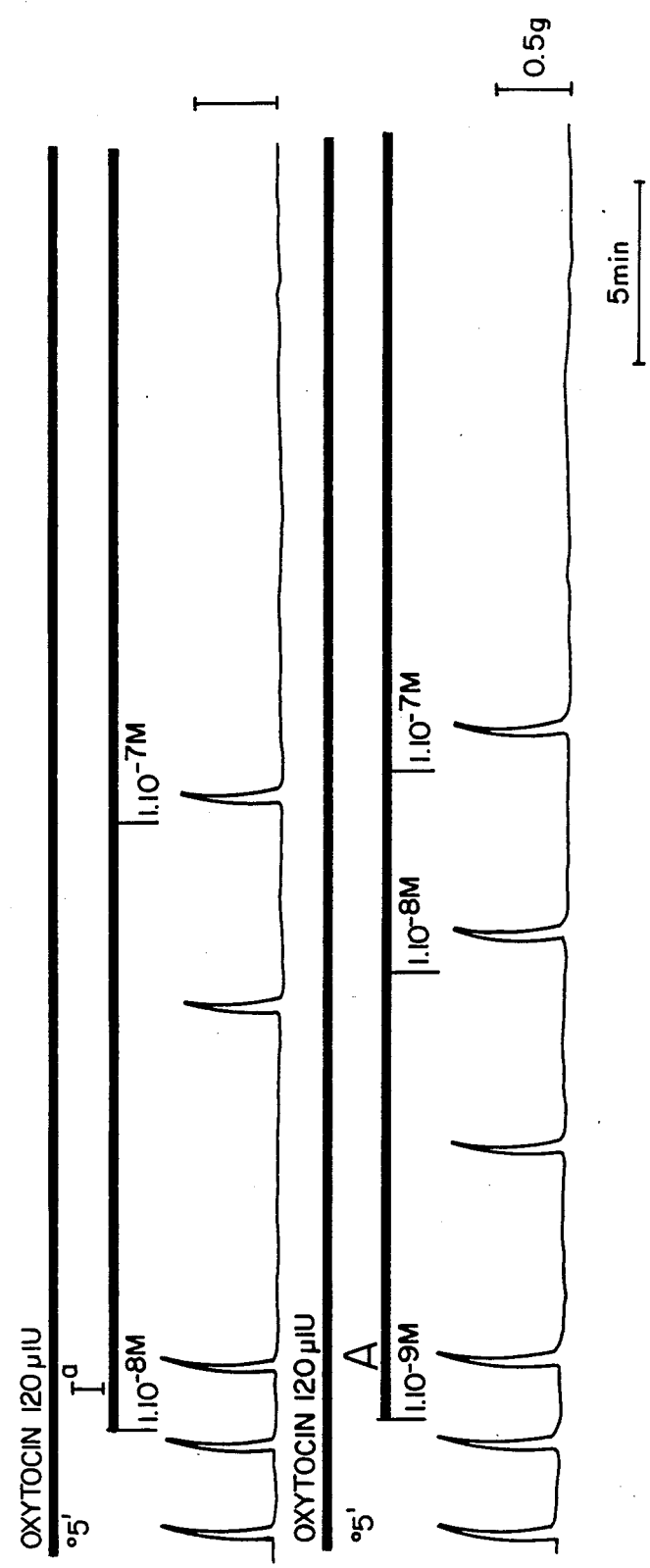
FIG. 2 represents the effect of compounds $I^a$ and A on the contractile activity of myometric strips, from rats, stimulated by oxytocin.

The isoquinoline derivative 1-1-(3,4,5-trimetoxybenzyl)-6,7-dihydroxy-1,2,3,4-tetrahydroisoquinoline (compound $I^a$) and the reference compound 1-(3,5 dihydrophenyl)-2-[(4-hydroxybenzyl)-ethyl-amino]-ethanol hydrobromide (compound A) were introduced cumulatively against a background of spontaneous activity and oxytocin and acetylcholine induced contractions. The cumulative acetylcholine curves were plotted against the background of both preparations (1 and A). Compound $I^a$ suppresses both spontaneous contractile activity (FIG. 1) and myometrium contraction promoted by oxytocin and acetylcholine (FIG. 2).

Compound $I^a$ suppresses spontaneous contraction at magnitudes of $1 \times 10^{-16}$ and $1 \times 10^{-18}$ mol; with complete suppression of oxytocin stimulation at concentrations of $1 \times 10^{-7}$ mol. Propanol, introduced in advance, removes the inhibiting effect of the compound.

Both inventive compound $I^a$ and reference compound A provoke a substantial drift to the right in the cumulative curves of acetylcholine, with paths that coincide.

Figure 3:
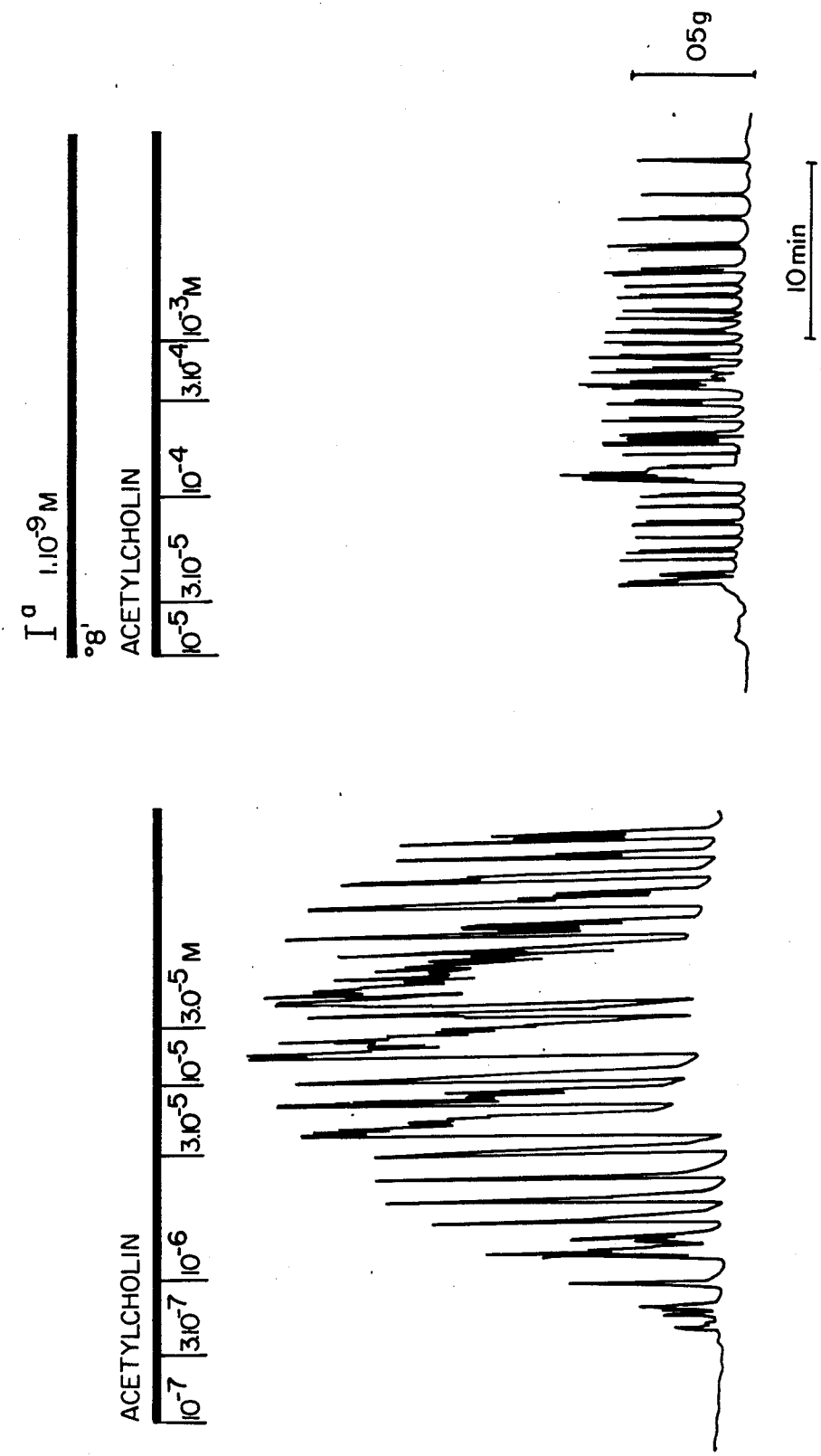
FIG. 3 represents the effect of compound $I^a$ ($1 \times 10^{-9}$) on the contractile response of myometric strips treated with acetylcholine.

When acetylcholine in excess of $1 \times 10^9$ mol is introduced over the background activity of compound $I^a$, an abrupt decrease in the acetylcholine contraction responce occurs, so much so that a cumulative curve cannot be plotted. See, FIG. 3.

Experiments on Conscious Dogs

Experiments were performed on conscious dogs according to the method described by Milenov, et al. *Bulletin of the Institute of Physiology*, Vol. IX (1965).

A. Influence of Compound $I^a$ on the mechanogram and myoelectric activity of the uterus.

Figure 4:
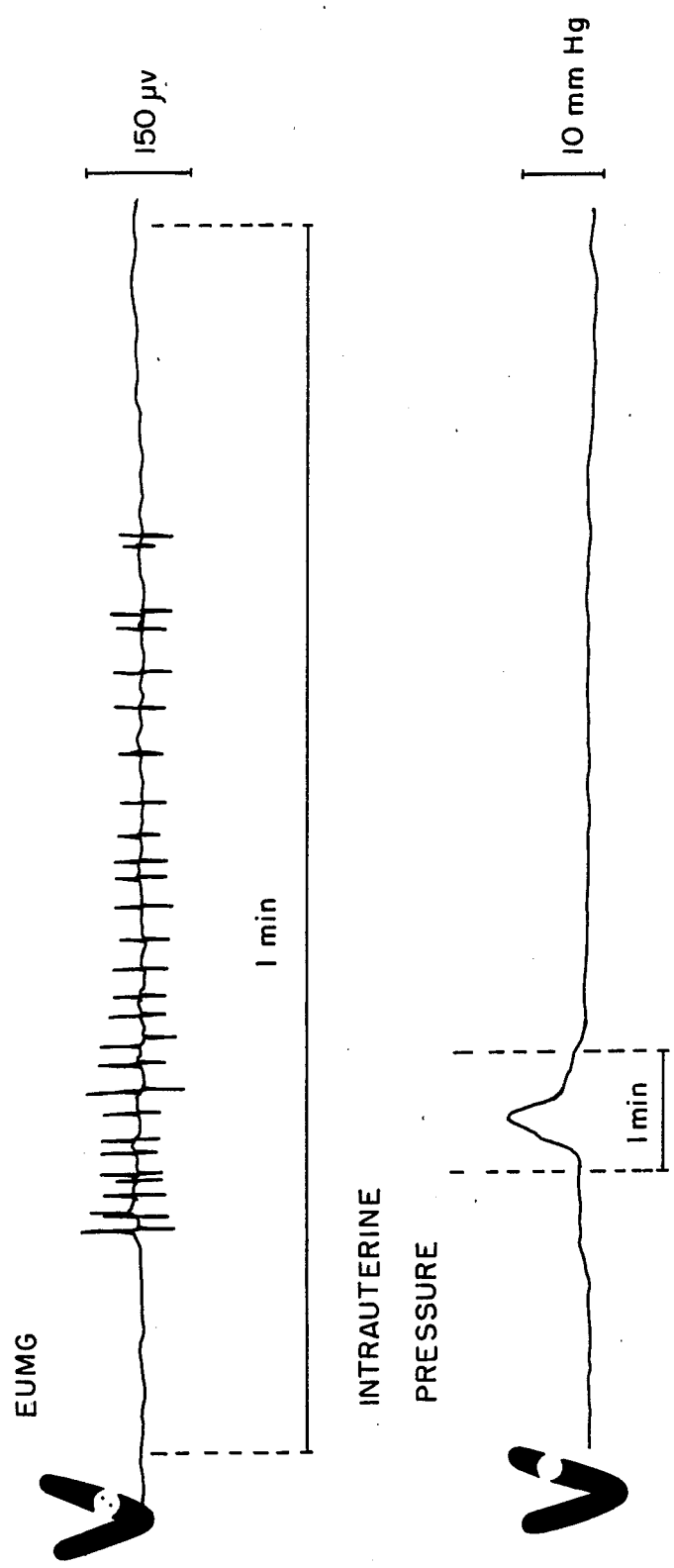
FIG. 4 represents the contractile activity of a dog uterus under chronic experimental conditions. Electrical activity and intrauterine pressure are recorded with different velocities.

The spontaneous activity of the uterus was recorded, and consists of groups of spikes having durations of 1 to 1.5 minutes (long spike groups) and groups of 15 to 60 seconds. The pace and contractile activity of the spike groups was recorded, and reflects changes in the intrauterine pressure. See, FIG. 4.

Figure 5:
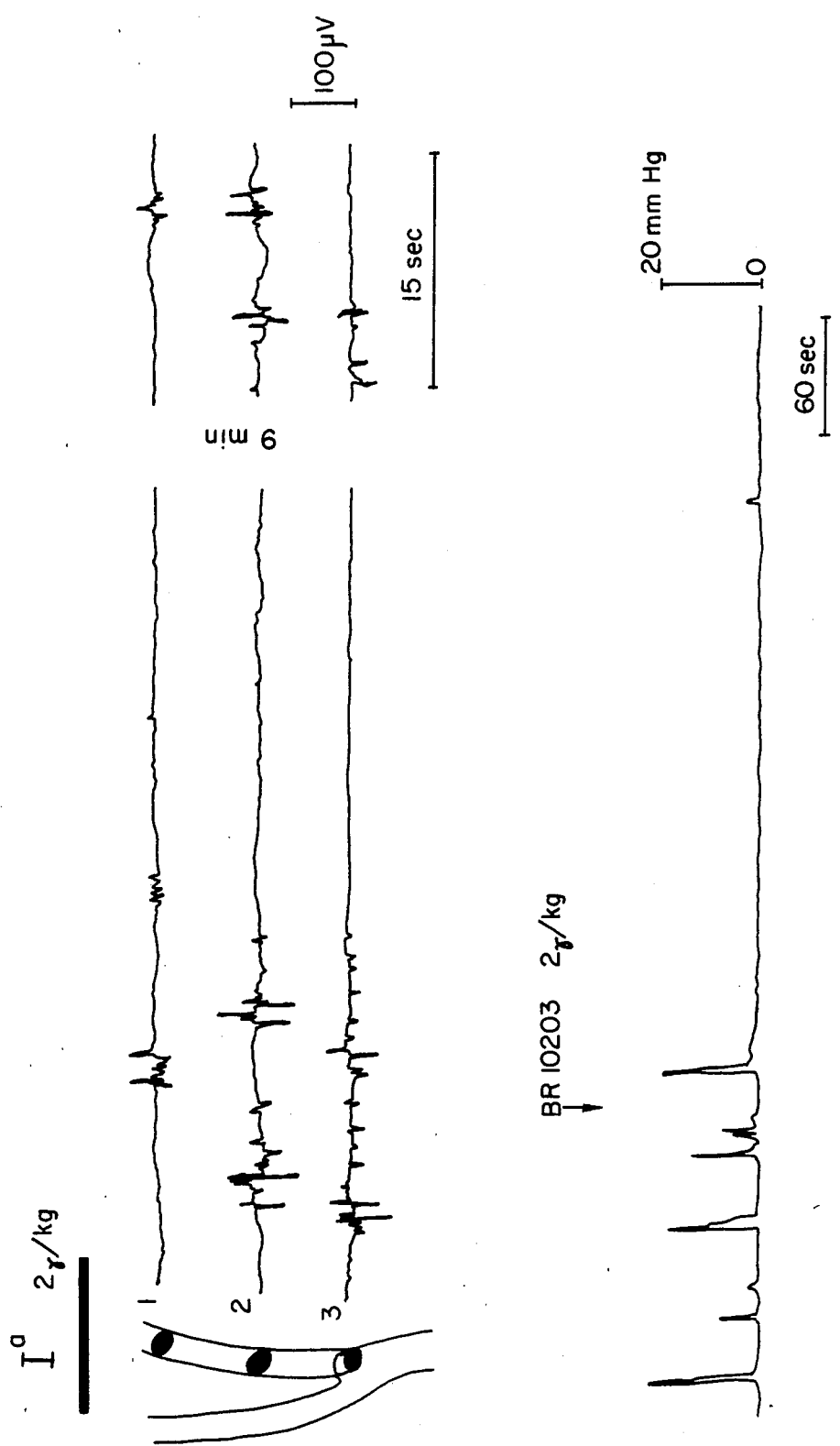
FIG. 5 represents the electrical activity (lead off- 1, 2, and 3) and contractile activity of a dog uterus prior to and after injection of compound $I^a$; with restoration of electrical activity after a 9 minute pause.
Figure 6:
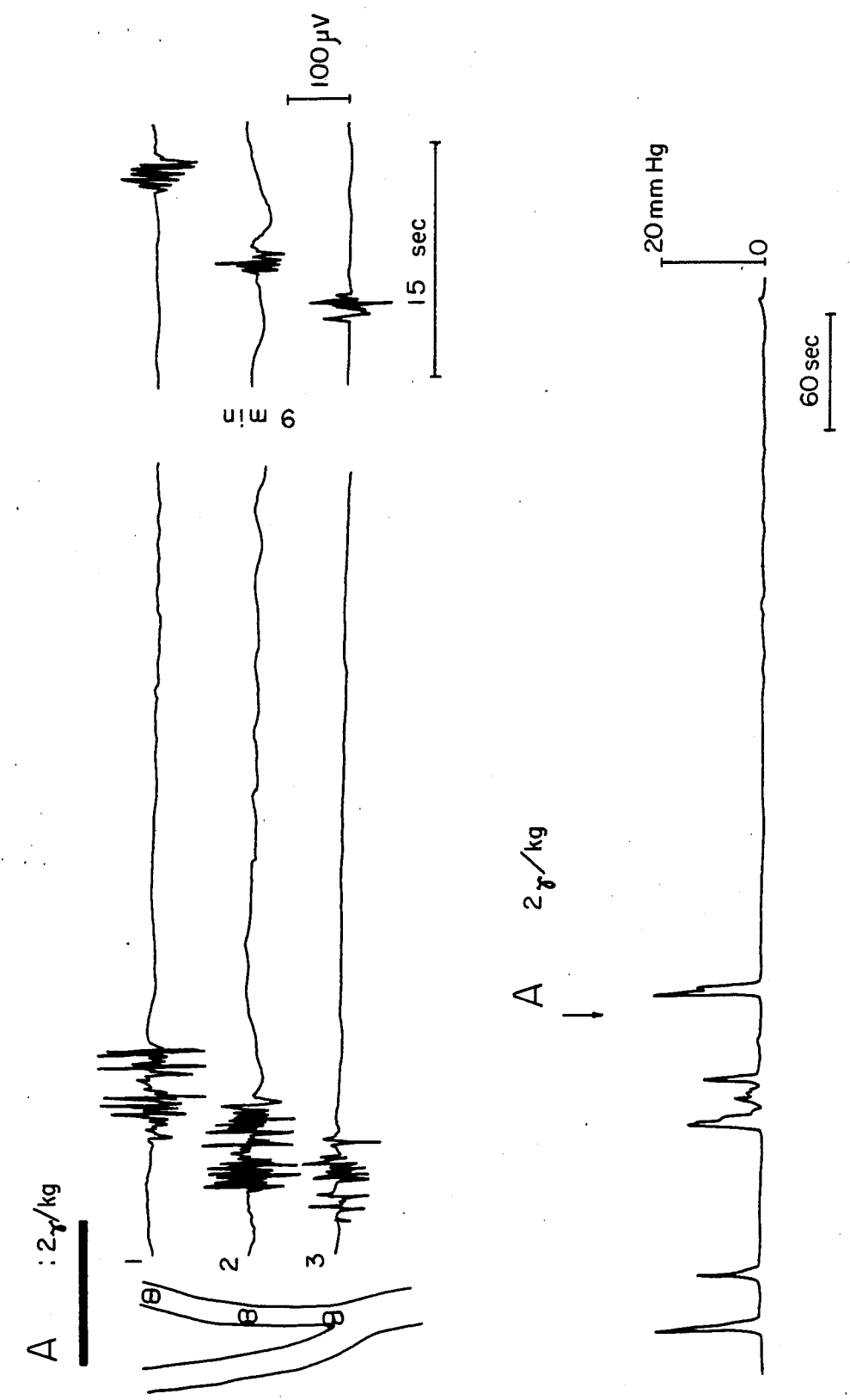
FIG. 6 represents the electrical activity (lead off- 1, 2, and 3) and contractile activity of a dog uterus prior to and after injection of compound A; with restoration of electrical activity after a 9 minute pause.

A dose of 1 mg/kg of compound $I^a$ was introduced, and resulted in total inhibition of myoelectric and contractile activity for a 3 to 6 minute period. This was followed by gradual restoration of activity over a period lasting from the 8th to the 10th minute. A dose of 2 mg/kg resulted in total inhibition of contractions and spike activity for a period of 8 to 10 minutes. See, FIG. 5. Gradual restoration of activity followed, with complete restoration occurring from the 12th to the 15th minute. Analogous effects were achieved with compound A, except that the inventive compound acted more rapidly than the reference compound. See, FIG. 6.

B. Influence of Compound $I^a$ on oxytocin-stimulated contractile and myoelectric activity of the uterus.

Intravenous administration of 0.06 MU/kg of oxytocin provokes an abrupt increase in the tonicity and amplitude of the mechanogram. In the electrouteromyogram the effect of oxytocin is expressed as continuous spike activity in the first 2–3 minutes, which later is broken by short pauses or rests lasting 5–10 seconds. See, FIG. 7. In the experiments described, oxytocin stimulation of the uterus dampened within 30 to 40 minutes after its introduction.

Figure 7:
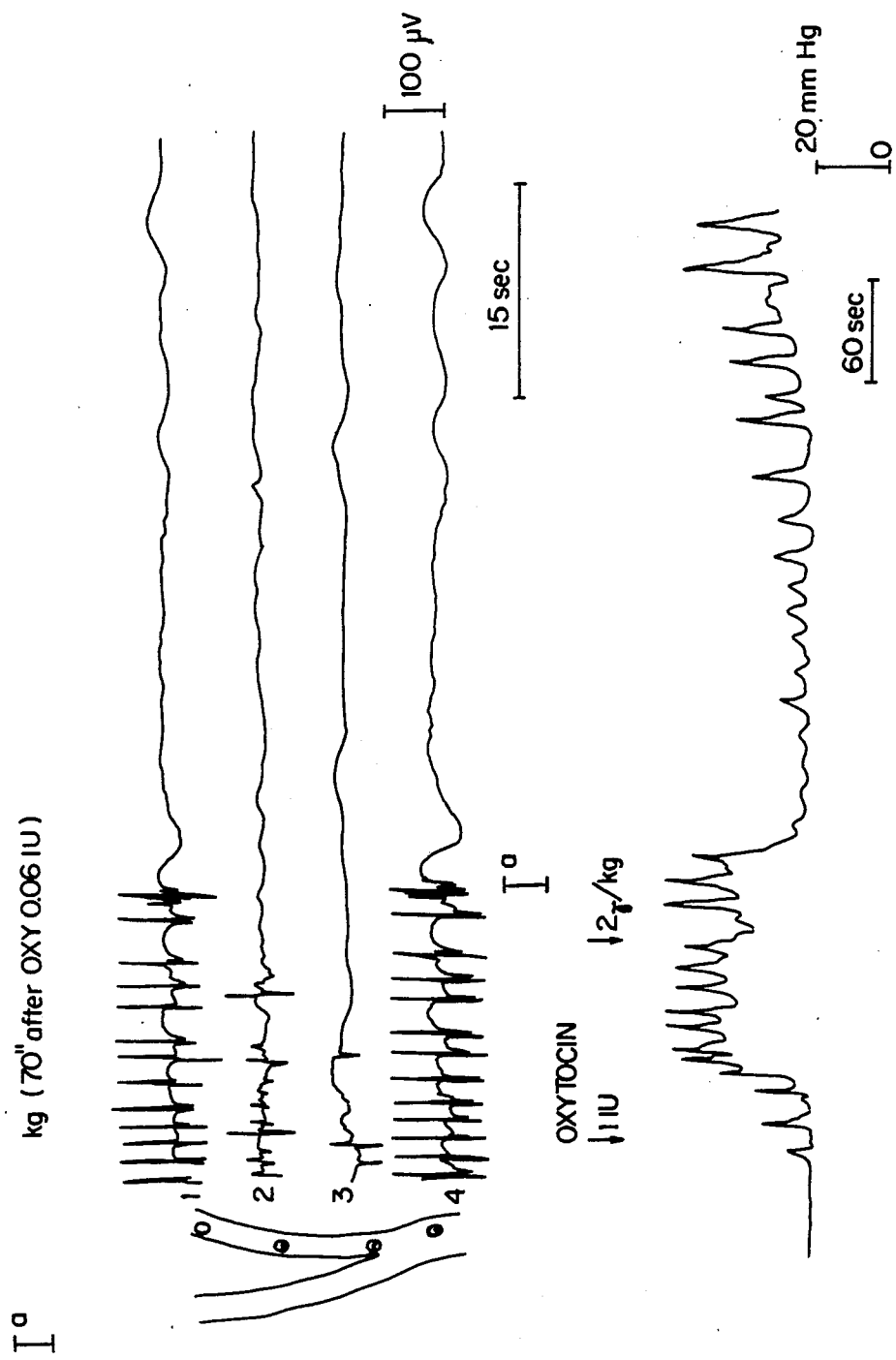
FIG. 7 represents the electrical activity (lead off- 1, 2, 3 and 4) and contractile activity under oxytocin stimulation, prior to and after injection of compound $I^a$. As shown, compound $I^a$ inhibits contractions when introduced over this background.

Compound $I^a$ was introduced over this background in a dose of 2 mkg/kg and resulted in distinct suppression of the contractile and spike activity in all of the experiments. FIG. 7.

C. Influence of Compound $I^a$ on animal behavior and pulse frequency.

Both the inventive compound $I^a$ and reference compound A each provoke an increase in pulse frequency during the first minutes after initial administration. For the inventive compound $I^a$, this effect is entirely dampened after 30 to 40 minutes. Compound A is dampened after 70 to 80 minutes. Additional injections with compound $I^a$, at higher doses, produces only a slight effect on pulse frequency and the animals show no change in behavior.

Experiments on Rabbits

Non-pregnant rabbits and rabbits pregnant for 20 days were tested against a background of spontaneous activity according to the method described by Milenov et al. *Bulletin of the Institute of Physiology*, Vol. IX (1965).

Figure 8:
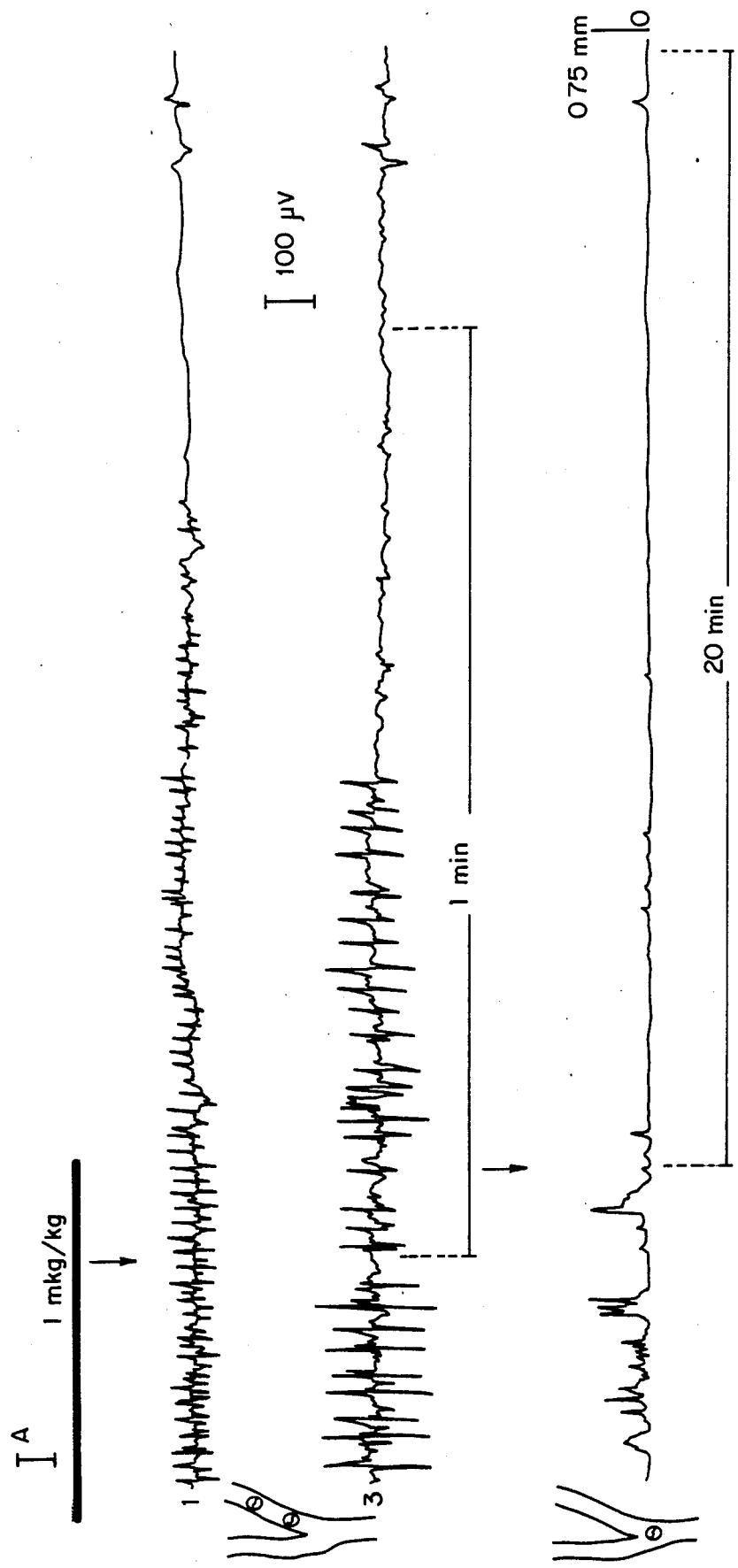
FIG. 8 represents the electrical activity (lead off- 1 and 3) and contractile activity of a non-pregnant rabbit prior to and after injection with compound $I^a$.
Figure 9:
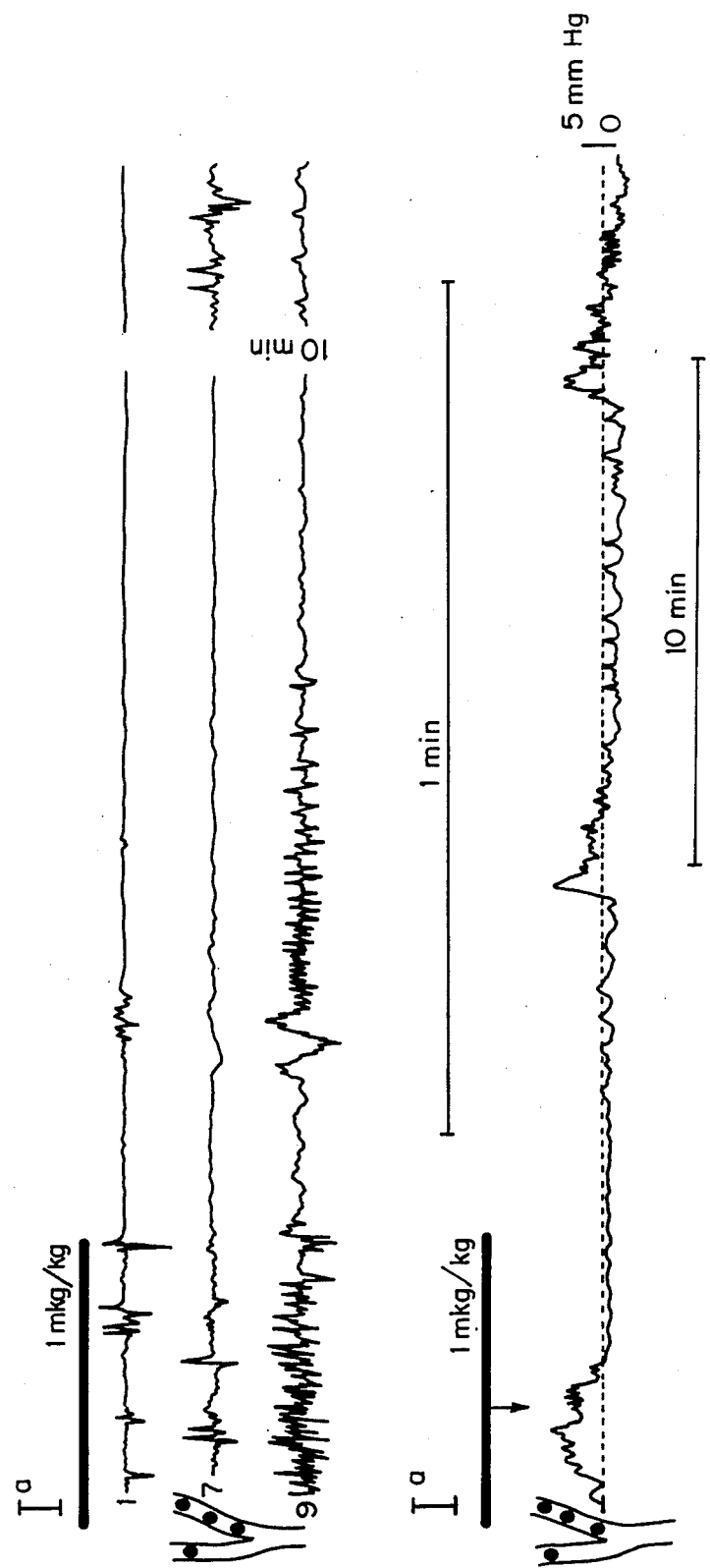
FIG. 9 represents the electrical activity (lead off- 1,7 and 9) and contractile activity of a pregnant rabbit prior to and after injection with compound $I^a$; with restoration of electrical activity after a 10 minute pause.

Compound $I^a$, dosed at 1 mgk/kg, suppresses myoelectric activity in pregnant and non-pregnant rabbits. See, FIG. 8 and 9. Compound $I^a$ also suppresses tonicity contractions and phasic contractions superimposed thereon. In pregnant animals, a simultaneous decrease in basal tonicity is observed, indicating strong relaxation of the uterine musculature.

Figure 10:
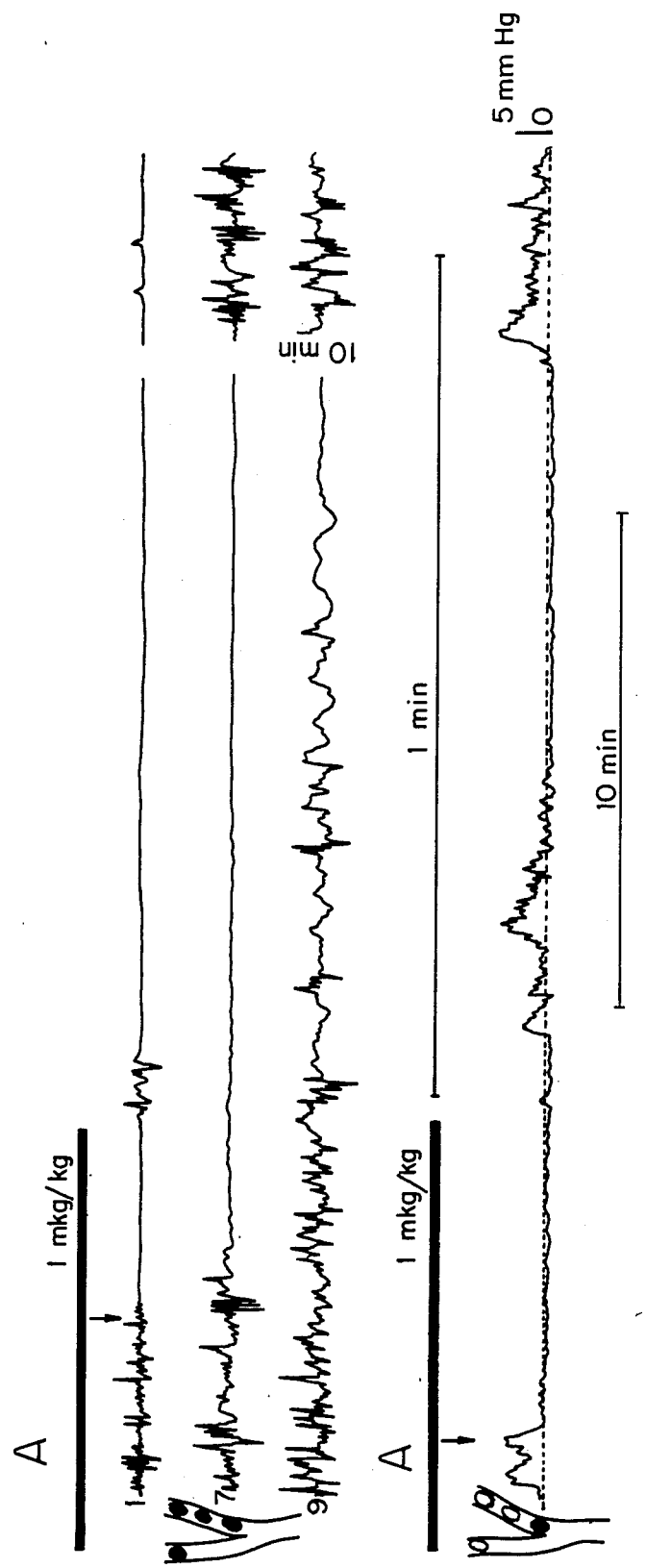
FIG. 10 represents the electrical activity (lead off- 1,7 and 9) and contractile activity of a pregnant rabbit prior to and after injection with compound A; with restoration of electrical and contractile activity after a 10 minute pause.

Compound A exhibits analogous results. However, the duration of the inhibition effect is shorter. See, FIG. 10.

Clinical Experiments

Compound $I^a$ was tested on 53 patients as a tocolytic means and obstetric relaxant in cases of spontaneous abortion and premature childbirth. Initial administration of the inventive compound was by intravenous drop infusion with glucose, for rapid shading of uterine contractions. Subsequent doses were administered orally, or by anal suppository.

The effect of the treatment on uterine contractions and the cardiac tones of the infant was determined by dynamic monitoring of a number of factors: the alkaline-acid status (AAS) of the pregnant patients and biological parameters relating to the mother's health, such as SMA 7, SMA 12, ECG, blood pressure, tolerance to the drug, pain, and other anamnestic data.

A comparison between compound $I^a$ and compound A reveals that compound $I^a$ successfully suppresses premature uterine contractions in pregnant women in 88% of the cases, while compound A is 85% successful. The alkaline-acid status control, in continuous infusion of compound $I^a$, indicates that there are no large deviations in fundamental biochemical parameters ($pO_2$, $pCO_2$, SB, BE, and pH). See, Table 1. Unlike compound A, there is no tendency toward metabolytic acidosis, and stabilization with Chromethanol is therefore unnecessary. See, Table 2.

The inventive compound is well tolerated by patients, and secondary effects (including accelerated activity) are minimal. No unfavorable effect on the fetus or adverse action on its cardiac frequency has been observed. No unfavorable effect on newborn infants has been observed.

It has been noted that the drug is more effective in suppressing pain and premature contractions when administered as a suppository rather than orally in the form of a pill.

The clinical dosage depends on the kind and degree of illness, and the manner of administration. In principal tocologic therapy, initial administration is in the form of a long intravenous infusion of the active compound at the rate of 1 to 5 micrograms/minute in an isotonic glucose or other physiological solution. In some cases, the infusion rate can be reduced to 0.6 to 4.0 micrograms/min. Subsequent treatment, as disclosed, is by oral administration of the active compound in doses of 9 to 20 mg/day or by suppositories dosed at 1 to 2 mg/day.

The following examples are illustrative of dosage forms suitable for the invention. It will be understood by skilled practitioners that these examples do not serve to limit the scope of the invention or the appended claims.

EXAMPLE 1 (Injection)

A 10 l stock solution suitable for injection can be prepared with the following ingredients:

| | |
|---|---|
| compound $I^a$ | 0.5 g |
| ascorbinic acid 99% | 2.0 g |
| sodium sulphite, anhydrous 100% | 1.0 g |
| sodium metabisulphite 100% | 1.0 g |
| sodium chloride 99.5% | 85.0 g |
| aqua for injections up to: | 10.0 l |

Fresh distilled water is boiled for 15 to 20 min. and is then saturated by barbotage (keeping the solution in inert medium) with pure nitrogen till cool. The following ingredients are consecutively dissolved in about 9 l of this saturated water by stirring: sodium sulphite, sodium metabisulphite, ascorbinic acid, sodium chloride, and compound $I^a$, with continuous nitrogen saturation. The solution is then filtered through a "Minipore" filter with a 0.45 membrane under nitrogen. The filtered solution is placed in an ampule under double gasing with nitrogen, followed by sterilization in a current of water vapor at 100° C. for 30 minutes.

EXAMPLE 2 (Suppositories)

The active ingredient (compound $I^a$) is crushed and combined with an inert filler or pharmaceutical excipient) to form a powdered mixture. An inert vehicle is melted and slowly combined with the powdered mixture to form a solution which is stirred until homogeneous. The solution is then fed into an automatic machine which forms suppositories. The final suppository contains from 0.1 to 0.5% of active ingredient.

EXAMPLE 3 (Pills)

A suitable pill can be prepared from the following components:

| | |
|---|---|
| compound $I^a$ | 0.003 g |
| lactic sugar | 0.035 g |
| wheat starch | 0.018 g |
| talc | 0.002 g |
| magnesium stearate | 0.001 g |
| gelatin | 0.001 g |
| TOTAL | 0.060 g |
| film coating | 0.003 g |

The active compound, lactic sugar, and part of the wheat starch are granulated with a 10% solution of gelatin. The resulting granules are dried to stable (rest) humidity of 2 to 3% and are then powdered with the remaining starch, talc and magnesium stearate. The entire mixture is processed into pills, which are coated with a film of acetone-based laquer.

TABLE 1

Mean values and standard deviation (+/−) of alkaline-acid activity indices and blood gases for 12 pregnant women exposed to continuous infusion of compoud $I^a$

| FACTOR | HOUR 0 | HOUR 1 | HOUR 2 | HOUR 3 | HOUR 4 | HOUR 10 |
|---|---|---|---|---|---|---|
| pH | 7.45 + −0.04 | 7.44 + −0.01 | 7.43 + −0.03 | 7.44 + −0.02 | 7.44 + −0.02 | 7.45 + −0.01 |
| BE | −6.1 + −1.9 | −6.7 + −2.4 | −7.9 + −2.7 | −6.3 + −2.6 | −6.3 + −2.6 | −6.3 + −3.00 |
| sB | 19.6 + −1.2 | 20.2 + −2.3 | 18.5 + −2.0 | 19.7 + −1.9 | 19.4 + −1.9 | 19.4 + −2.4 |
| $pCO_2$ | 23.0 + −2.5 | 23.2 + −2.4 | 22.4 + −3.00 | 23.2 + −3.2 | 23.3 + −3.6 | 23.2 + −3.5 |
| $pO_2$ | 84.4 + −8.9 | 90.4 + −17.8 | 96.0 + −21.2 | 89.8 + −20.3 | 82.2 + −9.9 | 82.4 + −14.5 |

TABLE 2

Mean values and standard deviation (+/−) of alkaline-acid activity indices and blood gases for 20 pregnant women exposed to continuous infusion of compound A

| FACTOR | HOUR 0 | HOUR 1 | HOUR 2 | HOUR 3 | HOUR 4 |
|---|---|---|---|---|---|
| pH | 7.44 + −0.04 | 7.41 + −0.04 | 7.43 + −0.05 | 7.43 + −0.03 | 7.44 + −0.04 |

TABLE 2-continued

Mean values and standard deviation (+/−) of alkaline-acid activity indices and blood gases for 20 pregnant women exposed to continuous infusion of compound A

| FACTOR | HOUR 0 | HOUR 1 | HOUR 2 | HOUR 3 | HOUR 4 |
|---|---|---|---|---|---|
| BE | −4.3 + −3.3 | −6.6 + −3.2 | −6.1 + −3.00 | −6.00 + −3.1 | −4.0 + −3.4 |
| sB | 21.8 + −3.9 | 19.1 + −3.1 | 19.5 + −2.2 | 19.7 + −2.2 | 20.3 + −2.8 |
| $pCO_2$ | 27.0 + −6.3 | 23.9 + −5.6 | 25.4 + −5.4 | 26.0 + −6.1 | 25.2 + −5.7 |
| $pO_2$ | 85.8 + −11.2 | 84.2 + −8.9 | 83.0 + −10.1 | 83.4 + −9.4 | 81.1 + −10.5 |

$pH = -\log[H_3O^+]$;
BE = basic excess;
sB = standard bicarbonates;
$pCO_2$ = partial pressure of $CO_2$; and
$pO_2$ = partial pressure of oxygen

We claim:

1. A method for therapeutic suppression of uterine contractions in mammalian females comprising the administration of a uterine contractions suppression effective amount, an active ingredient selected from the group consisting of a compound of the formula

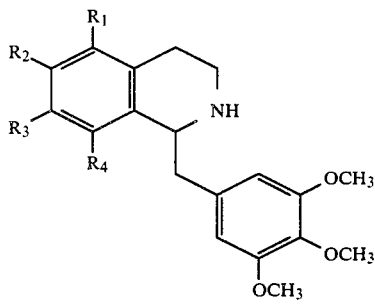

wherein $R_1$, $R_2$, $R_3$ and $R_4$ are each selected from the group consisting of a hydrogen and a hydroxyl group, and a pharmaceutical salt of a compound of this formula in combination with a pharmaceutical carrier.

2. A method according to claim 1 wherein the active ingredient is selected from the group consisting of 1-1-(3,4,5-trimetoxybenzyl)-6,7-dihydroxy-1,2,3,4-tetrahydroisoquinoline and its physiologically acceptable salts.

3. A method according to claim 1 wherein the active ingredient is orally dosed daily at from 9 to 20 milligrams.

4. A method according to claim 1 wherein the active ingredient is dosed parenterally at from 1 to 5 micrograms/minute.

5. A method according to claim 1 wherein the active ingredient is rectally dosed daily at from 1 to 2 milligrams.

6. A method according to claim 1 wherein the active ingredient is dosed first as an intravenous infusion at the rate of 1 to 5 micrograms/minute followed by subsequent administration in a daily dose selected from the group consisting of an oral dose of 9 to 24 milligrams and a rectal dose of 1 to 2 milligrams.

* * * * *